US008865917B2

(12) United States Patent
Wilson et al.

(10) Patent No.: US 8,865,917 B2
(45) Date of Patent: Oct. 21, 2014

(54) HARDENERS FOR THERMOSETTABLE RESIN COMPOSITIONS

(75) Inventors: Mark B. Wilson, Clute, TX (US); Stephanie L. Potisek, Pearland, TX (US); Ashwin Bharadwaj, Pearland, TX (US); Michael J. Mullins, Houston, TX (US); Steven J. Guillaudeu, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 182 days.

(21) Appl. No.: 13/699,141

(22) PCT Filed: May 12, 2011

(86) PCT No.: PCT/US2011/000844
§ 371 (c)(1),
(2), (4) Date: Nov. 20, 2012

(87) PCT Pub. No.: WO2011/146106
PCT Pub. Date: Nov. 24, 2011

(65) Prior Publication Data
US 2013/0066026 A1    Mar. 14, 2013

Related U.S. Application Data

(60) Provisional application No. 61/347,070, filed on May 21, 2010.

(51) Int. Cl.
| | |
|---|---|
| C07C 211/31 | (2006.01) |
| C07D 207/448 | (2006.01) |
| C08G 59/50 | (2006.01) |
| C08L 25/04 | (2006.01) |
| C08L 33/10 | (2006.01) |
| C08L 61/06 | (2006.01) |
| C08L 63/02 | (2006.01) |
| C08L 63/04 | (2006.01) |
| C08L 63/10 | (2006.01) |
| C08L 75/04 | (2006.01) |
| C07C 211/50 | (2006.01) |
| C08L 63/00 | (2006.01) |
| C08K 5/16 | (2006.01) |

(52) U.S. Cl.
CPC .......... *C07C 211/50* (2013.01); *C08G 59/5033* (2013.01); *C08L 63/00* (2013.01); *C07C 2101/18* (2013.01); *C08K 5/16* (2013.01); *C07C 2101/14* (2013.01); *C07C 2102/42* (2013.01); *C07C 2103/91* (2013.01); *C08G 59/504* (2013.01); *C07C 2103/68* (2013.01)
USPC ............... 548/549; 525/330.5; 525/333.6; 525/443; 525/456; 525/504; 525/523; 525/531; 528/122

(58) Field of Classification Search
None
See application file for complete search history.

(56) References Cited

U.S. PATENT DOCUMENTS

| | | | |
|---|---|---|---|
| 3,018,262 A | 1/1962 | Schroeder | |
| 3,291,775 A * | 12/1966 | Holm | ............... 528/121 |
| 3,499,933 A | 3/1970 | Pruett et al. | |
| 4,154,737 A | 5/1979 | Orphanides | |
| 4,579,957 A | 4/1986 | Kanayama et al. | |
| 4,775,735 A * | 10/1988 | Goel | ............... 528/90 |
| 4,845,305 A | 7/1989 | Meier | |
| 4,925,901 A | 5/1990 | Bertram et al. | |
| 5,112,989 A | 5/1992 | Yonemoto et al. | |
| 5,405,688 A | 4/1995 | Decker et al. | |
| 6,153,719 A | 11/2000 | Abbey et al. | |
| 6,541,445 B1 | 4/2003 | Markert | |
| 6,572,971 B2 | 6/2003 | Martin | |
| 6,632,893 B2 | 10/2003 | Konarski et al. | |
| 6,887,574 B2 | 5/2005 | Dean et al. | |
| 7,037,958 B1 | 5/2006 | Hansen et al. | |
| 7,163,973 B2 | 1/2007 | Ahsan | |
| 2005/0171237 A1 | 8/2005 | Patel et al. | |
| 2006/0293172 A1 | 12/2006 | Rubinsztajn et al. | |
| 2008/0075965 A1 | 3/2008 | Dershem | |

FOREIGN PATENT DOCUMENTS

| | | |
|---|---|---|
| EP | 0099268 | 1/1984 |
| EP | 0387381 | 9/1990 |
| EP | 0477677 | 4/1992 |
| JP | 62227920 | 10/1987 |
| WO | 0107382 | 2/2001 |
| WO | 2006052727 | 5/2006 |
| WO | 2008064115 | 5/2008 |
| WO | 2008153542 | 12/2008 |
| WO | 2009035838 | 3/2009 |
| WO | 2009114383 | 9/2009 |

OTHER PUBLICATIONS

International Search Report and Written Opinion from related PCT application PCT/US2011/000844 dated Sep. 20, 2011, 17 pages.
International Preliminary Report on Patentability from related PCT application PCT/US2011/000844 dated Aug. 7, 2012, 15 pages.
Guga, et al. "Oxathiaphospholane Approach to the Synthesis of P-Chiral, Isotopomeric Deoxy(ribonucleoside phosphorothioate)s and Phosphates Labeled with an Oxygen Isotope", Angew. Chem. Int. Ed., 2001, 40, No. 3, pp. 610-613.
Wilds, et al. "Steroid Analogs Lacking Ring C. V. Some Analogs of Testosterone and Androstenedione", Journal of the American Chemical Society, vol. 77, No. 3, 1955, pp. 647-651.

(Continued)

*Primary Examiner* — Robert Sellers
(74) *Attorney, Agent, or Firm* — Brooks, Cameron & Huebsch, PLLC

(57) ABSTRACT

A multifunctional aromatic amine hardener composition including the reaction condensation product of (a) at least one aniline and (b) at least one non-aromatic cyclic dicarboxaldehyde; and a reactive thermosettable resin composition including (i) at least one multifunctional aromatic amine hardener composition curing agent, (ii) at least one thermoset resin, and optionally (c) at least one catalyst; and a process for preparing a thermoset product from the thermosettable composition. The hardener composition above and a thermoset resin may be used to prepare a thermoset product with improved thermo-mechanical behavior.

6 Claims, No Drawings

(56) References Cited

OTHER PUBLICATIONS

Haldar, et al. "Thermolysis of N-aryl-B-chlorovinylimines : Synthesis of 7,13-Dibutyl-4-phenanthridino[3,2-a]-4-phenanthridino[2,3-j]anthracene, a novel cavity shaped nonacyclic diazaarene", SYNLETT, vol. 1997, No. 9. 1997. pp. 1057-1058.

Kawai, et al. "Dynamic Covalently Bonded Rotaxanes Cross-Linked by Imine Bonds between the Axle and Ring: Inverse Temperature Dependence of Subunit Mobility", Angew. Chem. Int. Ed. vol. 45, No. 26, 2006, pp. 4281-4286.

Lee, et al. "Handbook of Epoxy Resins", McGraw-Hill Book Company, New York, 1967, Chapter 2, pp. 2-1 to 2-33.

Chaudhuri, "A New Synthesis of Phthalaldehydes", J. Amer. Chem Soc., 64,1942, p. 315.

* cited by examiner

HARDENERS FOR THERMOSETTABLE RESIN COMPOSITIONS

This application is a National Stage application under 35 U.S.C. 371 of PCT/US2011/000844, filed on May 12, 2011 and published as WO 2011/146106 A1 on Nov. 24, 2011, which claims the benefit of U.S. Provisional Application Ser. No. 61/347,070 filed May 21, 2010, the entire contents of which are incorporated herein by reference in its entirety.

BACKGROUND OF THE INVENTION

1. Field of the Invention

The present invention is related to hardeners for thermosettable compositions; and more specifically, to a multifunctional aromatic amine useful as a curing agent for a thermoset resin such as an epoxy resin; and a process for preparing the thermosettable compositions.

The thermosettable compositions of the present invention are useful in various applications such as electrical, electronic, casting, potting, encapsulation, and composites.

2. Description of Background and Related Art

It is known to use thermosetting or thermoset resins such as epoxy resins in combination with curing agents to form thermoset cured products useful in various fields such as, for example, in the field of composites, electrical laminates and coatings. For some applications such as for manufacturing composites, electrical laminates and coatings, it is required to prepare and use a thermoset product with a high heat resistance (e.g. a glass transition temperature (Tg) of greater than 200° C.) in order for the thermoset product to be effective when used in a high temperature environment.

Aromatic amine hardeners commonly used in preparing thermosettable compositions include for example, methylene dianiline (also known as 4,4'-methanediyldianiline) [MDA], toluene diamine (TDA) and various alkylated derivatives. These known hardeners (also referred to as curing agents or crosslinking agents) impart a moderately high Tg value in the cured polymer. For example, the use of MDA with bisphenol A diglycidyl ether provides a thermoset with a Tg of 187° C., and the use of MDA with an epoxy novolac (e.g., D.E.N.™ 438) provides a thermoset with a Tg of 206° C. However, these known hardener materials have some volatility and undesirable toxicological characteristics that limit their use in some cases.

Polyaromatic amine hardeners derived from aromatic dialdehydes are also known (see e.g. Kanayama JP62227920 Chem. Abs. Ref. 108:132850). When polyaromatic amine hardeners derived from aromatic dialdehydes are used as curing agents with epoxy resins, heat distortion temperatures of as high as 286° C. are obtained compared to 167° C. using MDA. Heat distortion temperatures are typically within 20° C. (+/−) of the Tg, and therefore such hardeners would meet the needs of the industry. Unfortunately, the precursors for the polyaromatic amine hardeners, such as benzenedialdehydes, are difficult and expensive to prepare. For example, one common method to prepare the polyaromatic amine hardeners is to react benzaldehyde with chloroform in the presence of a strong base. This gives a mixture of bis-(dichloromethyl) benzaldehydes that can be converted to the dialdehydes with aqueous KOH (see e.g. Chaudhuri, J. Amer. Chem. Soc., 64, p. 315 (1942)). Other methods for preparing dialdehydes are described in U.S. Pat. No. 4,845,305. The overall yields of the dialdehydes from commercially available starting materials using these multi-step processes are unsatisfactory, and give numerous side-products. As a consequence, the benzene dialdehyde isomers (phthalaldehyde, isophthalaldehyde, and terephthalaldehyde) are only available as specialty chemicals and are quite expensive.

It is desired to provide a multifunctional aromatic amine hardener composition for thermoset resins such as epoxy resins which can impart a high Tg to the resulting cured thermoset product after cure and which can be prepared inexpensively.

SUMMARY OF THE INVENTION

One embodiment of the present invention is directed to a hardener composition, and more specifically to a multifunctional aromatic amine hardener for epoxy resins which imparts a high glass transition temperature (Tg) to the resulting cured product after cure. In one preferred embodiment, the multifunctional aromatic amine hardener includes aniline derivatives of cyclic carboxaldehydes useful for the manufacture of high glass transition polymers.

The multifunctional aromatic amine hardeners of the present invention are relatively non-volatile and give cured thermoset products with exceptionally high Tgs.

Another embodiment of the present invention is directed to the use of the above-described multifunctional aromatic amine hardener to prepare a reactive thermosettable resin composition including (a) at least one thermoset resin such as an epoxy resin, (b) the above multifunctional aromatic amine hardener composition of the present invention, and (c) optionally, at least one catalyst.

The thermosettable resin composition of the present invention may be used to prepare cured thermoset products with improved thermo-mechanical behavior.

Yet another embodiment of the present invention is directed to synthesizing and utilizing the above multifunctional aromatic amine hardener compositions. For example, in one particular embodiment of the process of the present invention, a novel tetrafunctional aromatic amine is prepared based on the reaction product of aniline and cyclohexane dicarboxaldehyde. The resultant tetrafunctional aromatic amine hardener advantageously imparts a high Tg value to a thermoset product when the tetrafunctional aromatic amine hardener is utilized as a curing agent for thermoset resins such as epoxy resins.

DETAILED DESCRIPTION OF THE INVENTION

In its broadest scope the present invention includes a multifunctional aromatic amine hardener comprising a reactive product of (a) at least one aniline compound; (b) at least one non-aromatic cyclic dicarboxaldehyde; and (c) optionally, in the presence of at least one catalyst. For example, the multifunctional aromatic amine hardener composition can be prepared by a reaction condensation process.

The hardener composition of the present invention, in turn, can be used to prepare a reactive curable or thermosettable resin composition, for example, a composition including (a) at least one thermoset resin, (b) the above multifunctional aromatic amine hardener composition, and (c) optionally, at least one catalyst. The reactive thermosettable resin composition of the present invention, in turn, may be used to prepare a cured thermoset product with improved thermo-mechanical behavior.

The present invention includes a multifunctional aromatic amine hardener composition prepared by reacting, for example, via a condensation reaction, (a) at least one aniline with (b) at least one non-aromatic cyclic dicarboxaldehyde; and (c) optionally, in the presence of at least one catalyst.

For example, the multifunctional aromatic amine hardener composition of the present invention may include a composition having the following chemical Structure (I):

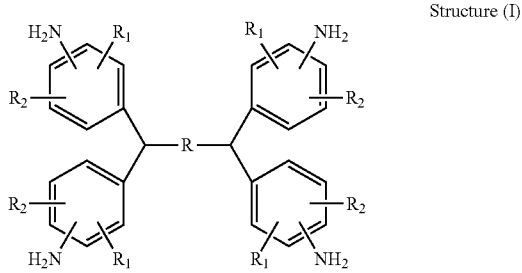

Structure (I)

wherein R in Structure (I) may be a cycloaliphatic diradical such as:

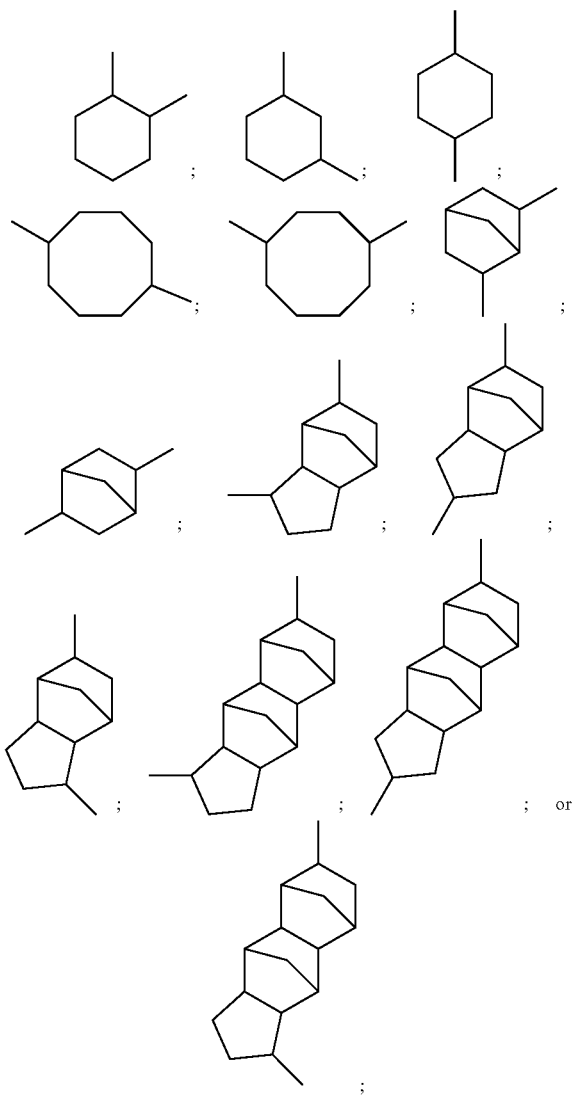

and $R_1$ and $R_2$ may be independently hydrogen, methyl, ethyl, i-propyl, n-propyl, n-butyl, i-butyl, t-butyl, methoxy, bromine, chlorine, fluorine, trifluoromethyl, methoxy, or ethoxy.

The multifunctional aromatic amine hardener composition of the present invention also may include a maleimide composition derived from the multifunctional aromatic amine hardener composition having the following Structure (II):

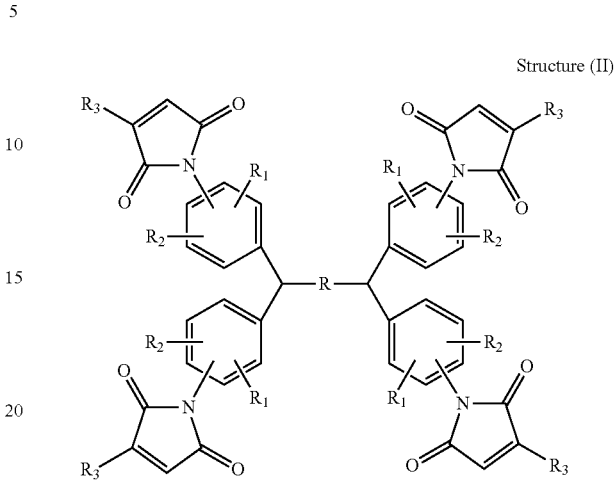

Structure (II)

wherein R, $R_1$, and $R_2$ are as described above; and $R_3$ may be hydrogen or a hydrocarbon radical containing from 1 to about 6 carbons.

As aforementioned, the present invention includes a multifunctional aromatic amine hardener composition prepared, for example, by a condensation reaction of (a) at least one aniline, (b) at least one non-aromatic cyclic dicarboxaldehyde; and (c) optionally, at least one catalyst. For example, the multifunctional aromatic amine hardener composition of the present invention is prepared by condensing dialdehydes with anilines.

The aniline material, component (a), useful in preparing the multifunctional aromatic amine hardener composition of the present invention can be any known aniline compound suitable for reacting with an aldehyde. For example, the aniline may include o-toluidine; m-toluidine; p-toluidine; o-ethylaniline; p-ethylaniline; 2,4-dimethylaniline; 2,6-dimethylaniline; 2,4-diethylaniline; 2,6-diethylaniline; o-isopropylaniline; p-butylaniline; 4-aminoindane; 5-aminoindane; o-anisidine; o-phenetidine; chloroanilines; bromoanilines; 1-aminonaphthalene; 2-aminonaphthalene; other aromatic amines; and mixtures thereof.

Dianilines such as methylene dianiline (also known as 4,4'-methanediyldianiline) [MDA] and toluene diamine (TDA) can also be used as the aniline material, component (a), but these dianilines may lead to oligomeric products which may be undesirable in some applications due to the viscosity increase caused by the oligomeric products. In other embodiments, small amounts (e.g. less than about 70%) of the above dianilines in combination with monoanilines may also be used in some reaction mixtures.

The cyclic dicarboxaldehyde material, component (b), useful in preparing the amine hardener composition of the present invention, can be any known cyclic dialdehyde of the formula OHC—R—CHO wherein R is as defined above. Such dialdehydes can be prepared by hydroformylation of olefins and diolefins. Several specific non-limiting examples are shown below. The combination of a Diels-Alder reaction between acrolein and a conjugated diene is particularly expedient. For example, butadiene reacts with acrolein to form a cyclohexane carboxaldehyde that can be converted to the dialdehyde by hydroformylation with hydrogen and carbon monoxide as described in WO 2001007382 and WO 2009035838. A description of a typical hydroformylation process useful in the present invention is found in, for example, pages 13-22 of WO 2009035838. The following Equations (I) and (II) further describe the hydroformylation process:

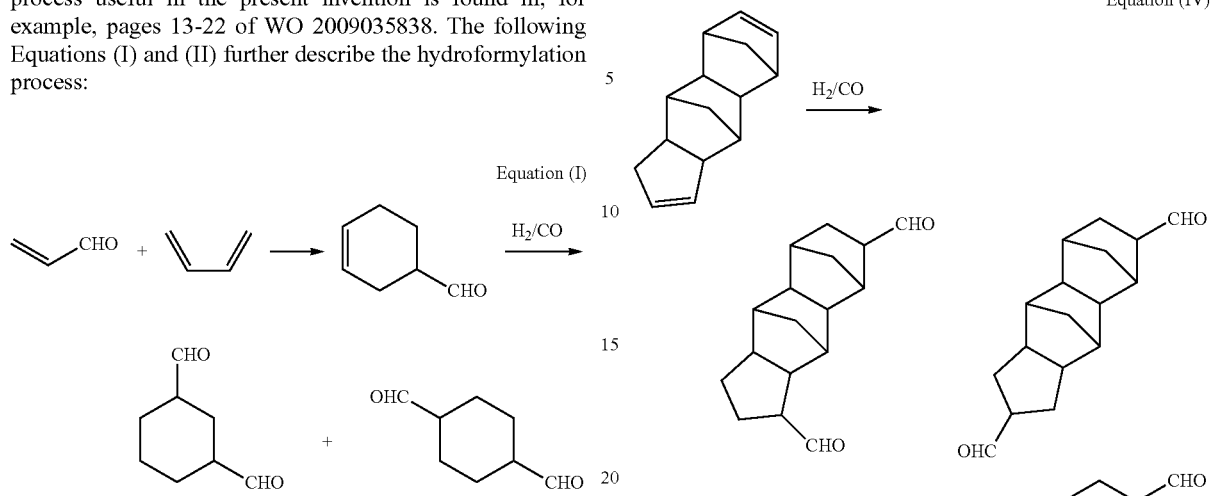

The above same strategy can be used with cyclopentadiene to produce norbornane dialdehydes in two steps as follows:

Alternatively, it is possible to directly hydroformylate cyclic diolefins such as cyclohexadiene, cyclooctadiene, cyclododecadiene, norbornadiene (bicycle[2.2.1]hepta-2,5-diene), dicyclopentadiene, and tricyclopentadiene using a similar process as described in U.S. Pat. Nos. 6,541,445 and 3,499,933 as shown in the reaction schemes Equations (III)-(VI) below.

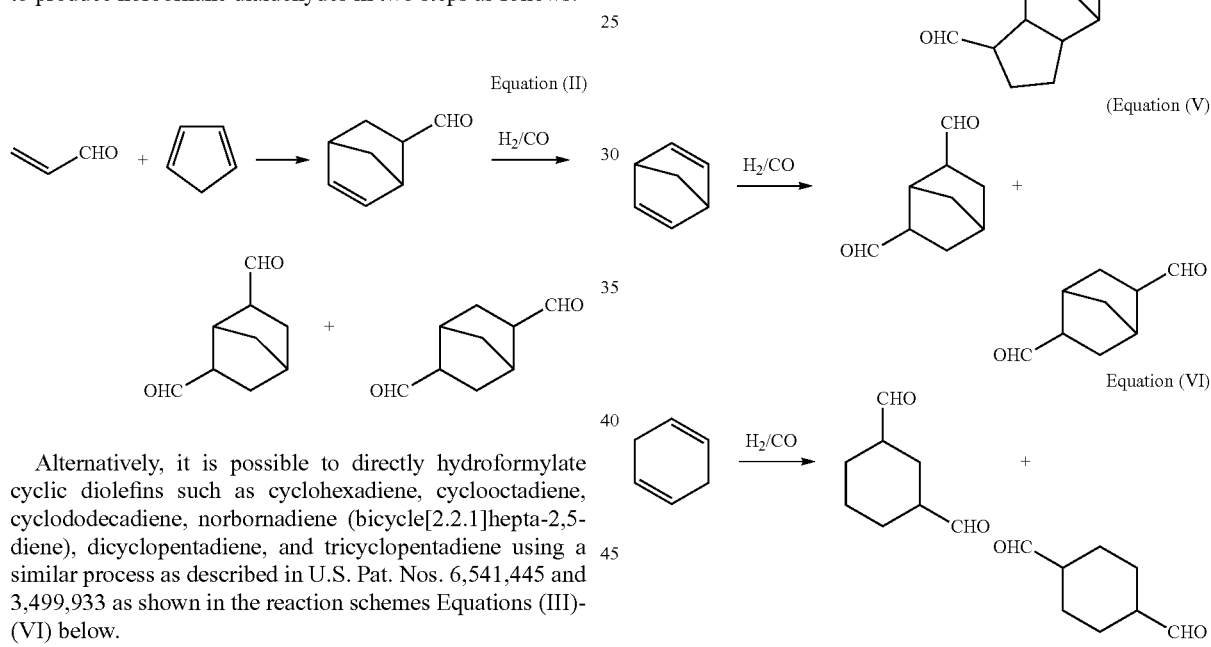

The above equations provide process steps that proceed in excellent yield under conditions that are easily achieved, and therefore these dialdehyde precursors shown in Equations (I)-(VI) above can be produced inexpensively. Thus, the multifunctional aromatic amine hardener of the present invention can be produced inexpensively yet deliver high performance.

As aforementioned, the process for producing the multifunctional aromatic amine hardener composition of the present invention includes the step of condensing dialdehydes with anilines. This condensation reaction is performed by combining the reactants in a molar ratio of aniline to dialdehyde of generally from about 4:1 to about 20:1 molar ratio (aniline:dialdehyde) at elevated temperature, optionally in the presence of a catalyst. The molar ratio of aniline to dialdehyde is generally from about 4:1 to about 20:1, preferably from about 4:1 to about 12:1, and more preferably from about 4:1 to about 8:1. As a general rule, the lower the mole ratio, the higher the molecular weight (Mw) of the product. This occurs because it is believed that the product competes with the aniline starting material, and oligomers are formed. This occurs more particularly as the reaction proceeds since the aniline starting material is consumed as the reaction proceeds. High ratios of aniline to dialdehyde give products with lower molecular weights (less oligomers), but excess aniline remains after the reaction and may have to be removed.

The condensation reaction temperature may be in the range of about 50° C. to 250° C., more preferably in the range of about 80° C. to about 180° C., and most preferably in the range of about 100° C. to about 160° C. The temperature of the condensation reaction may be increased or decreased as desired to increase product yield, decrease side products, and/or speed or slow the reaction time.

As an optional step, the product resulting from the condensation reaction may be purified using any well known purification processes such as for example column chromatography, distillation, and crystallization.

As an illustration of one embodiment of the present invention, the temperature of the condensation reaction of aniline with cyclohexane dicarboxaldehydes can be generally from about 40° C. to about 200° C., preferably from about 50° C. to about 150° C., and more preferably from about 80° C. to about 130° C.

The condensation reaction of aniline with cyclohexane dicarboxaldehydes may be carried out for a pre-determined reaction time of generally from about 30 minutes to about 24 hours, preferably from about 1 hour to about 12 hours, and more preferably from about 2 hours to about 6 hours.

Water may be a co-product of the reaction process of the present invention, and any water formed may be advantageously removed as the reaction proceeds. Any water formed may be removed by well known processes such as by direct distillation of water or as an azeotrope with the aniline or with an added solvent. When an azeotrope is used, the water can be separated by various means, such as drying or phase separation, and the dried aniline or solvent can be returned to the reaction vessel. Suitable solvents are preferably non-reactive with both starting materials, and have boiling points of at least about 80° C. For example, suitable solvents useful in the present invention include benzene, toluene, xylene, ethylbenzene, mesitylene, chlorobenzene, decalin, mixed aliphatic hydrocarbons, and mixtures thereof.

The reaction of the present invention may be carried out above or below atmospheric pressure (1 bar), but atmospheric pressure is preferred. An inert gas may be used to reduce the oxidation of the aniline, which can produce dark colored by-products. For example, nitrogen is preferably used as the inert gas when an inert gas is used.

In one embodiment, for example, the conversion of each aldehyde group into a methylene dianiline derivative proceeds through an imine (R—C=N—R') intermediate. For example, this is the product of one aniline with one aldehyde, producing water as a co-product. As the reaction proceeds, these imines are converted to the ultimate products by reaction with an additional mole of aniline. Although some unconverted imine is tolerable in the final product, it is generally desirable to minimize the amount of unconverted imine. Preferably the molar ratio of imine to moles aldehyde in the starting dialdehyde is less than about 50%, more preferably less than about 35%, and most preferably less than about 25%.

Generally, the process of producing the multifunctional aromatic amine hardener composition of the present invention, i.e., the condensation of anilines with dialdehydes may be carried out in the presence of a condensation catalyst as an optional component (c).

For example, in one embodiment, the amines of the present invention may be prepared by condensing cyclohexyl carboxaldehydes with aniline (or a derivative of an aniline) in the presence of a strong protic or Lewis acid condensation catalyst. Suitable strong protic acids useful in the present invention include, for example, HCl, sulfuric, arylsulfonic, phosphoric acid or mixtures thereof. HCl is preferably used. Suitable Lewis acid condensation catalysts useful in the present invention include for example, $ZnCl_2$, $SnCl_2$, $SnCl_4$, $AlCl_3$, $BF_3$, or mixtures thereof. It is possible to use an aniline salt of the above condensation catalysts such as anilinium chloride, sulfate, bisulfate, phosphate, arylsulfonate, and the like, or mixtures thereof.

The concentration of the condensation catalyst used for preparing the amine hardener composition ranges generally from 0 mol % to about 100 mol % (ratio of moles of catalyst to moles of dialdehyde), preferably from about 0.01 mol % to about 50 mol %, and more preferably from about 0.1 mol % to about 5 mol % based on the total weight of the composition.

If an acid condensation catalyst is used in the present invention, after the reaction is complete, the acid catalyst may be neutralized with yet another optional component, a base, such as a hydroxide, a carbonate, a phosphate or mixtures thereof to form a salt which is readily removable. Once the salts are removed from the resulting mixture by washing or other removing means, the resultant crude mixture can be directly used as a hardener in preparing the thermosettable composition, or the crude mixture may be isolated into its individual components using well known means such as precipitation or chromatography.

The amine hardener composition product produced by the process of the present invention may also comprise a complicated mixture of poly(aromatic amines) that is useful as a hardener. For example, a few specific embodiments of the amine hardener composition of the present invention are shown by the following chemical Equations (VII) and (VIII) and the structures therein:

Equation (VII)

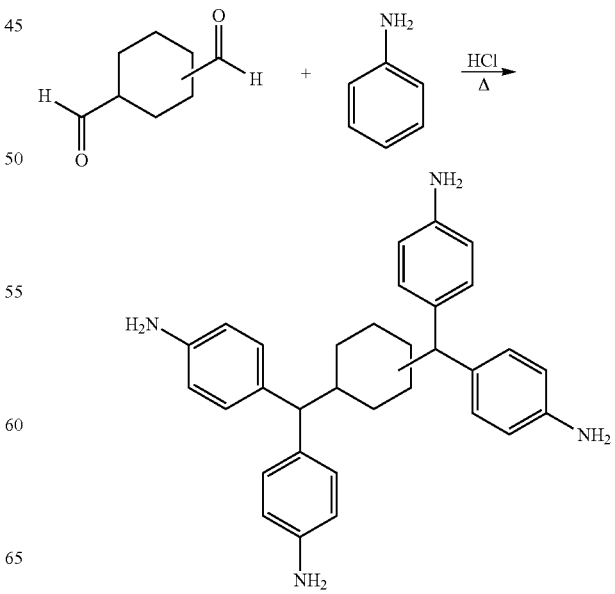

Equation (VIII)

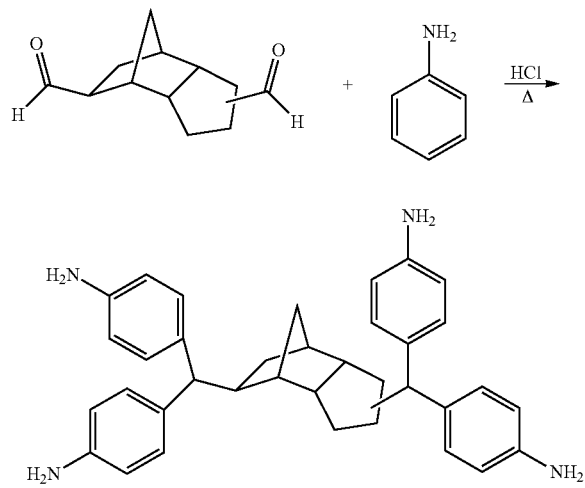

In Equations (VII) and (VIII) above, the products shown are only one of the components present in the reaction mixture making up the multifunctional aromatic amine hardener of the present invention. Other components may include for example ortho-anilines (only the para-anilines are shown above), imines, oligomers produced when the aldehyde starting material condenses with the product, and other condensation products.

The present invention also includes maleimide compositions derived from the multifunctional aromatic amine hardeners of the present invention. These maleimides are useful as thermoset monomers either by themselves or in combination with other classes of monomers such as epoxies, cyanates, benzoxazines, oxazolines, styrenes, acrylates, and 'active hydrogen' curing agents such as phenolics and anilines.

In one embodiment, to prepare the maleimide composition, the conversion process as shown in the following Equation (IX), can be performed by treating the multifunctional aromatic amine hardener composition with maleic anhydride (optionally substituted with $R_3$ which can be a hydrocarbon with 6 or fewer carbons).

Equation (IX)

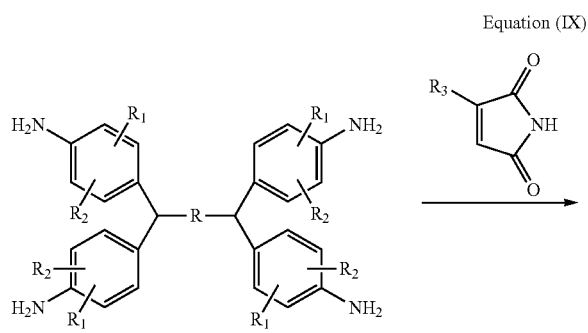

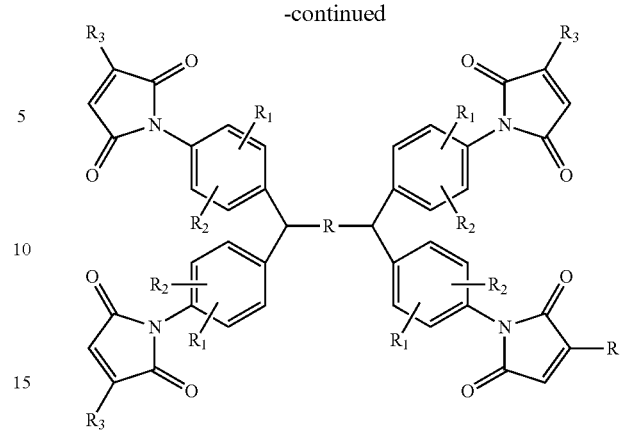

The above chemistry generates water that should be removed by physical or chemical means to drive the reaction to completion (for example, see the discussion in U.S. Patent Application Publication No. US20080075965A1; and U.S. Pat. No. 4,154,737). Physical methods for the removal of water may include, for example, distillation of water, preferably with a solvent such as toluene that forms an azeotrope with water. Chemical methods for the removal of water may include, for example, adding anhydrides such as acetic anhydride, orthoesters such as $MeC(OMe)_3$ or orthocarbonates such as $(MeO)_4C$ (see for example U.S. Pat. No. 5,112,989). Further details of water removal processes can also be found in U.S. Pat. No. 4,579,957 and EP 387,381.

Another embodiment of the present invention is directed to a thermosettable resin composition containing, as one component, the multifunctional aromatic amine hardeners of the present invention. For example, in one embodiment of the present invention, the thermosettable resin composition may include the multifunctional aromatic amine hardener material (a hardener herein may also be referred to herein interchangeably as a curing agent) blended with a thermoset resin such as an epoxy resin to form the thermosettable resin composition; wherein the hardener assists in curing the thermoset resin in the composition to form a cured thermoset product.

Therefore, the present invention includes as another broad embodiment a reactive thermosettable resin composition comprising (i) at least are multifunctional aromatic amine hardener composition as described above, (ii) at least one thermoset resin, such as an epoxy resin, and (iii) optionally, at least one curing catalyst.

In general, the reactive thermosettable resin composition of the present invention comprises (i) the multifunctional aromatic amine hardener composition of the present invention as described above, as the curing agent; and (ii) at least one thermoset resin, such as for example, at least one epoxy resin. The thermosettable composition herein may also be referred to herein interchangeably as the "system" or the "formulation".

The formulations of the present invention can be cured to produce a thermoset product with a high heat resistance (e.g. a glass transition temperature (Tg) of greater than 200° C.); and therefore, the formulations are useful for applications wherein the formulations may be subjected to high temperatures.

The multifunctional aromatic amine hardener described above may be used as component (i) for preparing a thermosettable resin composition. The thermosettable composition or formulation of the present invention may contain the multifunctional aromatic amine hardener composition as the hardener component in the thermosettable resin formulation in a range of from about 0.01% to about 100%, preferably greater than about 50% or more preferably greater than about 85%.

The use of the aromatic amines hardeners of the present invention in combination with a thermoset resin such as an epoxy resin can provide thermosets with extremely high Tgs. As an illustration of the present invention, the amines from cyclohexane dialdehyde [structure shown in Equation (VII)] cured with a polyglycidyl ether of a phenolic novolac (D.E.N.® 438, f=3.6) forms a thermoset with a Tg of 256° C. when cured at 220° C. In comparison, the amines from cyclohexane dialdehyde [structure shown in Equation (VII)] cured with standard bisphenol A based epoxy resin (e.g. D.E.R.® 332), exhibit a Tg of 229° C.

The thermoset resin, component (ii), useful in the thermosettable resin composition of the present invention may be selected from thermoset resins known in the art including at least one resin selected from epoxy resins; isocyanate resins; (meth)acrylic resins; phenolic resins; vinylic resins; styrenic resins; polyester resins; melamine resins; vinylester resins; maleimide resins; and mixtures thereof. Preferably, an epoxy resin is used as component (ii) in the thermosettable resin composition of the present invention.

In preparing the thermosettable resin composition of the present invention at least one epoxy resin, component (ii), is blended with the thermosettable resin composition to prepare aromatic amine hardener. Epoxy resins are those compounds containing at least one vicinal epoxy group. The epoxy resin may be saturated or unsaturated, aliphatic, cycloaliphatic, aromatic or heterocyclic and may be substituted. The epoxy resin may also be monomeric or polymeric. An extensive enumeration of epoxy resins useful in the present invention is found in Lee, H. and Neville, K., "Handbook of Epoxy Resins," McGraw-Hill Book Company, New York, 1967, Chapter 2, pages 257-307; incorporated herein by reference.

The epoxy resins, used in embodiments disclosed herein for component (ii) of the present invention, may vary and include conventional and commercially available epoxy resins, which may be used alone or in combinations of two or more. In choosing epoxy resins for compositions disclosed herein, consideration should not only be given to properties of the final product, but also to viscosity and other properties that may influence the processing of the resin composition.

Particularly suitable epoxy resins known to the skilled worker are based on reaction products of polyfunctional alcohols, phenols, cycloaliphatic carboxylic acids, aromatic amines, aminophenols or mixture thereof, with epichlorohydrin. A few non-limiting embodiments include, for example, bisphenol A diglycidyl ether, bisphenol F diglycidyl ether, resorcinol diglycidyl ether, triglycidyl ethers of para-aminophenols, and mixtures thereof. Other suitable epoxy resins known to the skilled worker include reaction products of epichlorohydrin with o-cresol and phenol novolacs, repectively. It is also possible to use a mixture of two or more of the above epoxy resins.

The epoxy resins, component (ii), useful in the present invention for the preparation of the curable compositions, may be selected from commercially available products. For example, D.E.R.® 331, D.E.R. 332, D.E.R. 354, D.E.R. 560, D.E.N.® 431, D.E.N. 438, D.E.N. 439, D.E.R. 736, or D.E.R. 732 available from The Dow Chemical Company may be used. As an illustration of the present invention, the epoxy resin component (a) may be a liquid epoxy resin, D.E.R. 383 [a diglycidylether of bisphenol A (DGEBPA)] having an epoxide equivalent weight of 175-185, a viscosity of 9.5 Pa-s and a density of 1.16 gms/cc. Other commercial epoxy resins that can be used for the epoxy resin component can be D.E.R. 330, D.E.R. 354, or D.E.R. 332.

Other suitable epoxy resins useful as component (ii) are disclosed in, for example, U.S. Pat. Nos. 3,018,262; 7,163,973; 6,887,574; 6,632,893; 6,242,083; 7,037,958; 6,572,971; 6,153,719; and 5,405,688; PCT Publication WO 2006/052727; and U.S. Patent Application Publication Nos. 20060293172 and 20050171237, each of which is hereby incorporated herein by reference.

In general, the equivalent ratio of epoxy to aniline can vary from about 2.0:1.0 to about 0.5:1.0, preferably from about 1.2:1.0 to about 0.8:1.0, more preferably from about 1.1:1.0 to about 0.9:1.0, and most preferably from about 1.050:1.0 to about 1.005:1.0. In general, the highest crosslink density results with a slight excess such as for example, from about 1.050:1.0 to about 1.005:1.0 of the epoxy, and this corresponds to the highest Tg.

An optional component useful in the thermosettable composition of the present invention includes at least one curing catalyst, component (iii). The curing catalyst useful in the present invention may be adapted for polymerization, including homopolymerization, of the at least one thermoset resin. Alternatively, the curing catalyst useful in the present invention may be adapted for catalyzing the reaction between the at least one thermoset resin and the at least one curing agent.

The curing catalyst useful in the present invention may include catalysts well known in the art. Examples of suitable catalysts useful for the thermosettable resin composition of the present invention may include compounds containing amine, phosphine, heterocyclic nitrogen, ammonium, phosphonium, arsonium, sulfonium moieties, and any combination thereof. The curing catalyst may include for example heterocyclic nitrogen-containing compounds and amine-containing compounds. The amine and phosphine moieties in the curing catalysts may be tertiary amine and phosphine moieties; and the ammonium and phosphonium moieties may be quaternary ammonium and phosphonium moieties. Among the tertiary amines that may be used as curing catalysts are those mono- or polyamines having an open-chain or cyclic structure which have all of the amine hydrogen replaced by suitable substituents, such as hydrocarbyl radicals, and preferably aliphatic, cycloaliphatic or aromatic radicals. Examples of suitable heterocyclic nitrogen-containing curing catalysts useful in the present invention include those described in U.S. Pat. No. 4,925,901; incorporated herein by reference.

Heterocyclic secondary and tertiary amines or nitrogen-containing curing catalysts which can be employed herein include, for example, imidazoles, benzimidazoles, imidazolidines, imidazolines, oxazoles, pyrroles, thiazoles, pyridines, pyrazines, morpholines, pyridazines, pyrimidines, pyrrolidines, pyrazoles, quinoxalines, quinazolines, phthalozines, quinolines, purines, indazoles, indoles, indolazines, phenazines, phenarsazines, phenothiazines, pyrrolines, indolines, piperidines, piperazines, and any combination thereof or the like. Especially preferred are the alkyl-substituted imidazoles; 2,5-chloro-4-ethyl imidazole; and phenyl-substituted imidazoles, and any mixture thereof. Examples of the most preferred embodiments of the curing catalysts useful in the present invention include N-methylimidazole; 2-methylimidazole; 2-ethyl-4-methylimidazole; 1,2-dimethylimidazole; 2-methylimidazole and imidazole-epoxy reaction adducts. More preferred embodiments of the curing catalysts include for example 2-phenylimidazole, 2-methylimidazole and 2-methylimidazole-epoxy adducts.

Embodiments of the curing catalyst suitable for the present invention include tertiary amines such as, for example, triethylamine, tripropylamine, tributylamine, 2-methylimidazole, benzyldimethylamine, 2-phenyl imidazole, 1-benzyl-2-phenyl imidazole (1B2PZ), imidazole derivative, 1,8-diazabicyclo[5.4.0]undec-7-ene (DBU), 2-methyl imidazole-epoxy adduct, such as EPON™ P101 (available from Hexion Chemical), isocyanate-amine adduct (available from Degussa); and any combination thereof.

Embodiments of quaternary phosphonium and ammonium compounds useful as the curing catalyst in the present invention include, for example, ethyltriphenylphosphonium chloride, ethyltriphenylphosphonium bromide, ethyltriphenylphosphonium iodide, ethyltriphenylphosphonium acetate, ethyltriphenylphosphonium diacetate (ethyltriphenylphosphonium acetate.acetic acid complex), ethyltriphenylphosphonium tetrahaloborate, tetrabutylphosphonium chloride, tetrabutylphosphonium acetate, tetrabutylphosphonium diacetate (tetrabutylphosphonium acetate.acetic acid complex), tetrabutylphosphonium tetrahaloborate, butyltriphenylphosphonium tetrabromobisphenate, butyltriphenylphosphonium bisphenate, butyltriphenylphosphonium bicarbonate, benzyltrimethylammonium chloride, benzyltrimethylammonium hydroxide, benzyltrimethylammonium tetrahaloborate, tetramethylammonium hydroxide, tetrabutylammonium hydroxide, tetrabutylammonium tetrahaloborate, and mixtures thereof.

Other suitable curing catalysts include ammonium compounds such as, for example, triethylammonium chloride, triethylammonium bromide, triethylammonium iodide, triethylammonium tetrahaloborate, tributylammonium chloride, tributylammonium bromide, tributylammonium iodide, tributylammonium tetrahaloborate, N,N-dimethyl-1,2-diaminoethane.tetrahaloboric acid complex, and mixtures thereof.

Other suitable curing catalysts include quaternary and tertiary ammonium phosphonium, and arsonium adducts or complexes with suitable non-nucleophilic acids such as, for example, fluoboric, fluoarsenic, fluoantimonic, fluophosphoric, perchloric, perbromic, periodic, and mixtures thereof.

The concentration of the curing catalyst present in the thermosettable resin composition ranges generally from about 0.01 weight percent (wt %) to about 5 wt %, preferably from about 0.05 wt % to about 2 wt %, and more preferably from about 0.1 wt % to about 1 wt % based on the total organic compounds in the composition. Above the about 5 wt % range, the reaction may be too fast (the reaction is a strong exotherm which can degrade the material) leading possibly to poor processability; and thus, the formulation may not be processed under conventional processing conditions. Below the about 0.01 wt % range, the reaction may be too slow prolonging the curing time; and thus, the formulation may not be processed under conventional processing conditions.

The selection of the curing catalyst useful in the present invention is not limited and commonly used catalysts for epoxy systems can be used. Also, the addition of an optional curing catalyst may depend on the system prepared. When the curing catalyst is used, preferred examples of the catalyst include tertiary amines, imidazoles, organo-phosphines, and acid salts.

Most preferred curing catalysts include tertiary amines such as, for example, triethylamine, tripropylamine, tributylamine, 2-methylimidazole, benzyldimethylamine, mixtures thereof, and the like.

Another optional component useful in the thermosettable composition of the present invention may include at least one optional co-curing agent. The co-curing agents, (also referred to as a co-hardener or co-cross-linking agent) useful in the thermosettable composition, may be selected, for example, from those curing agents well known in the art including, but are not limited to, anhydrides, carboxylic acids, amine compounds, phenolic compounds, polyols, or mixtures thereof.

As an illustration of one embodiment wherein the thermoset resin comprises an epoxy resin, at least one optional co-curing agent may be selected from amines, phenolic resins, carboxylic acids, carboxylic anhydrides, or mixtures thereof.

As an illustration of one embodiment wherein the thermoset resin comprises an isocyanate, the at least one optional co-curing agent may be selected from at least one polyol.

Examples of the optional co-curing agent useful in the present invention include any of the curing materials known to be useful for curing epoxy resin based compositions. Such materials include, for example, polyamine, polyamide, polyaminoamide, dicyandiamide, polyphenol, polymeric thiol, polycarboxylic acid and anhydride, polyol, tertiary amine, quaternary ammonium halide, and any combination thereof or the like. Other specific examples of the optional co-curing agent include dicyandiamide, phenol novolacs, bisphenol-A novolacs, phenol novolac of dicyclopentadiene, diphenylsulfone, styrene-maleic acid anhydride (SMA) copolymers; and any combination thereof.

Preferably, the optional co-curing agent used in the present invention may include for example dicyandiamide, substituted guanidines, phenolic, amino, benzoxazine, anhydrides, amido amines, polyamides, and mixtures thereof.

Dicyandiamide may be one preferred embodiment of the optional co-curing agent useful in the present invention because dicyandiamide has the advantage of providing delayed curing since dicyandiamide requires relatively high temperatures (e.g. greater than 120° C.) for activating its curing properties; and thus, dicyandiamide can be added to an epoxy resin and stored at room temperature (about 25° C.).

Among the optional conventional epoxy co-curing agents, amines and amino- or amido-containing resins are preferred. Solid epoxy co-curing agents at ambient temperature (about 25° C.) may be advantageously dissolved in a solvent to form a liquid co-curing agent.

The amount of the optional co-curing agent for the epoxy resin is usually such that the equivalent ratio of a functional group having an active hydrogen in the curing agent (the total amount of active hydrogens from the amine hardener composition and from the co-curing agent) to the epoxy groups in the epoxy resin in the total reactive epoxy resin composition is from about 0.2:1 to about 5:1, preferably from about 0.5:1 to about 2:1, and more preferably from about 0.9:1 to about 1.1:1 Below the ratio of 0.2:1 and above the ratio of 5:1, the glass transition temperature of the network may become lower, or the reactive functions may remain in the network and may increase the water absorption in humid environment; and generally, no networks may be obtained.

The thermosettable composition of the present invention may optionally contain one or more other additional optional additives which are useful for their intended uses. For example, the optional additives useful in the present invention composition may include, but not limited to, stabilizers, surfactants, flow modifiers, pigments or dyes, matting agents, degassing agents, flame retardants (e.g., inorganic flame retardants, halogenated flame retardants, and non-halogenated flame retardants such as phosphorus-containing materials), toughening agents, curing initiators, curing inhibitors, wetting agents, colorants or pigments, thermoplastics including polyphenylene oxide, processing aids, UV blocking compounds, fluorescent compounds, UV stabilizers, inert fillers, fibrous reinforcements, antioxidants, impact modifiers including thermoplastic particles, and mixtures thereof. The above list is intended to be exemplary and not limiting. The preferred additives for the, formulation of the present invention may be optimized by the skilled artisan.

The concentration of the optional additional additives is generally between about 0 wt % to about 50 wt %, preferably between about 0.01 wt % to about 20 wt %, more preferably between about 0.05 wt % to about 15 wt %, and most preferably between about 0.1 wt % to about 10 wt % based on the weight of the total composition. Below about 0.01 wt %, the additives generally do not provide any further significant advantage to the resultant thermoset product; and above about 20 wt %, the properties improvement brought by these additives remains relatively constant.

In various embodiment of the present invention, some of the optional additives used in the composition include for example, a halogen containing or halogen free flame retardant; a synergist to improve the performance of the flame out ability such as for example including magnesium hydroxide, zinc borate, metalocenes; a solvent for process ability such as for example acetone, methyl ethyl ketone, Dowanol PMA; functional or non-functional particulate fillers with a particle size range of 0.5 nm to 1000 μm such as for example silica, alumina trihydrate, aluminum oxide, aluminum hydroxide oxide, metal oxides, nano tubes; an adhesion promoter such as for example modified organosilanes (epoxidized, methacryl, amino), acetylacetonates, sulfur-containing molecules; a wetting and/or dispersing aid such as for example modified organosilanes, Byk 900 series and W 9010, modified fluorocarbons; an air release additive such as for example Byk A530, Byk A525, Byk A555, Byk A 560; a surface modifier such as for example slip and gloss additives (a number from Byk-Chemie); a reactive or non-reactive thermoplastic resin such as for example polyphenylsulfones, polysulfones, polyethersolufones, polyvinylidene fluoride, polyetherimide, polypthalimide, polybenzimidiazole, acyrlics, phenoxy, urethane; a mold release agent such as for example waxes; and other functional additives or prereacted products to improve polymer properties such as isocyanates, isocyanurates, cyanate esters, allyl containing molecules or other ethylenically unsaturated compounds or acrylates; or mixtures of any of the above additives.

The process for producing the thermosettable resin composition of the present invention includes admixing the above components of the formulation of the present invention. The components may be admixed in any order to provide the thermosettable composition of the present invention. All the components of the thermosettable epoxy resin composition are typically mixed and dispersed at a temperature enabling a low viscosity for the effective uniform mixing of the hardener composition with the epoxy resin. The temperature during the mixing of all components may be at ambient temperature; or from about 20° C. to about 90° C., and more preferably from about 50° C. to about 80° C. Any volatile by-products during mixing can be removed by vacuum degassing. Above the temperature of about 90° C., the crosslinking reaction may prematurely start during the mixing of components, and below the temperature of about 20° C., the viscosity of the composition may be too high to thoroughly and homogeneously mix the components together.

While the order of mixing is not critical under most processing conditions when a liquid amino hardener is used, in some instances, for example when a solid amino co-curing agent is used such as aromatic amines including for example diaminodiphenyl sulfone (DDS), diaminodiphenyl methane (DDM), m-phenylenediamine (mPDA), diaminodiphenyl ether, alkylated aromatic amines, dicyandiamide, the epoxy resin and the solid co-curing agent should first be mixed together at a high temperature (e.g., from about 120° C. to about 130° C.) to mix the co-curing agent homogeneously with the other components; and then the amine hardener of the present invention may be added at a lower temperature (e.g., from about 20° C. to about 90° C.) because the functional groups, i.e. the amino groups, on the amine hardener composition are very reactive.

In another embodiment, a solvent may be used to solubilize the aldehyde component or to increase reflux temperature. For example, the solvent may include N,N-dimethylformamide (DMF), dichlorobenzene, chlorobenzene, ethanol, ethyl acetate, methanol, chloroform, nitrobenzene, and mixtures thereof.

The process for producing the cured thermoset product of the present invention includes curing the reactive thermosettable resin formulation of the present invention. The thermosettable resin formulation can be cured under conventional processing conditions to form a thermoset. The resulting thermoset displays high Tgs (for example, greater than about 200° C.); and therefore, displays high use temperatures.

The process to produce the thermoset products of the present invention may be performed by gravity casting, vacuum casting, automatic pressure gelation (APG), vacuum pressure gelation (VPG), infusion, filament winding, lay up injection, transfer molding, prepreging, dipping, coating, spraying, brushing, and the like.

Curing the thermosettable composition may be carried out for a predetermined period of time sufficient to cure the composition. For example, the curing time may be chosen between about 1 minute to about 96 hours, preferably between about 5 minutes to about 48 hours, and more preferably between about 10 minutes to about 24 hours. Below a period of time of 1 minute, the time may be too short to enable mixing and molding of the composition; and above 96 hours, the time is too long to be practical or economical.

The final thermoset product produced by curing the thermosettable resin composition of the present invention displays excellent properties such as for example superior Tg (glass transition temperature) when compared to known cured resin products. The cured thermoset resin product of the present invention is therefore useful for applications where the thermoset has to endure high temperatures and/or temperature cycling. Temperatures above the Tg generally cause a dramatic drop in modulus and an increase in thermal expansion that can cause failure.

The end-use applications for the multifunctional aromatic amine hardener and the thermosettable resin composition containing such hardener of the present invention may include for example, electrical, electronic, potting, encapsulation, composite, or other applications where a high Tg thermoset is desirable. In addition, the aromatic amine hardener-containing thermosettable resin compositions can be used in combination with, or as a replacement for, high performance polyimides or polyurethanes.

As further illustrations of end uses for the epoxy resin compositions of the present invention; in general, the en uses include epoxy-type impregnating compounds useful for casting, potting, encapsulation, molding, and tooling. The present invention is particularly suitable for all types of electrical casting, potting, and encapsulation applications; for molding and plastic tooling; and for the fabrication of epoxy based composites parts, particularly for producing large epoxy-based parts produced by casting, potting and encapsulation. The resulting composite material may be useful in some applications, such as electrical casting applications or electronic encapsulations, castings, moldings, potting, encapsulations, injection, resin transfer moldings, composites, coatings and the like.

EXAMPLES

The following examples and comparative examples further illustrate the present invention in detail but are not to be construed to limit the scope thereof.

In the following examples, cyclohexane carboxaldehyde, aniline, 2-ethyl, 4-methyl imidazole, concentrated hydrochloric acid, 4,4'methanediyldianiline, and the 50% aqueous sodium hydroxide were obtained from Sigma-Aldrich. The samples of cyclohexane dicarboxaldehyde, dicyclopentadiene (DCPD) dialdehyde, D.E.N.® 438EK85 and D.E.R.® 332 (trademarks of The Dow Chemical Company) were obtained from The Dow Chemical Company.

The following standard analytical equipments and method was used in the Examples wherein: Tg was measured using a differential scanning calorimetry (DSC) (TA Instruments 2920 DSC) with a nitrogen purge of 50 cubic centimeters per minute (cc/min). A 5-10 mg sample was heated to 300° C. using a 20° C./minute ramp. The sample was then cooled to 50° C. and the heating ramp was repeated. The half extrapolated tangents analysis method was utilized to calculate the Tg.

Comparative Example A

The synthesis of an amine hardener composition was carried out as follows: Cyclohexane carboxaldehyde (5 g, 44.6 mmol, 1 equiv) and aniline (12.5 g, 134.3 mmol, 3 equiv) were added to a 100 mL two-necked round bottom flask equipped with a condenser and thermocouple. The flask was placed under nitrogen and 0.25 mL concentrated HCl was added. After refluxing at 110° C. for 5 hours, the reaction was allowed to cool to 50° C. and 0.75 mL of 50 wt % aqueous NaOH was added. Ethyl acetate (EtOAc) was added and the solution was washed with water (3×30 mL). The organic layer was dried over $MgSO_4$, filtered, and the solvent removed in vacuo. The resulting mixture contained residual aniline. Purification of the material was performed via column chromatography (66:33 hexane:EtOAc) to yield a tacky yellow solid, 4,4'-(cyclohexylmethylene)dianiline [Structure (XI)], Rf=0.25.

The following analytical data was obtained for the product synthesized in Comparative Example A:

$^1$H NMR (CDCl$_3$): d 7.02 (d, 2H), 6.58 (d, 2H), 3.25 (d, 1H), 1.93 (m, 1H), 1.60 (m, 4H), 1.17 (m, 4 H), 0.80 (m, 2H). MS (ESI): m/z calculated for C19H22N2+H, 281.3. Found: 281.2. IR (neat): n=3349 (br), 2918, 2848, 1619, 1510, 1270.

Example 1

The synthesis of an amine hardener composition was carried out as follows: Cyclohexane dicarboxaldehyde (24.43 g, 174 mmol, 1 equiv) and aniline (80.32 g, 862 mmol, 5.0 equiv) were added to a 250 mL two-necked round bottom flask equipped with a condenser and thermocouple. The flask was placed under nitrogen and 3.75 mL of concentrated hydrochloric acid was added gradually. After refluxing at 110° C. for 5 hours, the reaction was allowed to cool to 50° C. and 40 mL of 50 wt % aqueous sodium hydroxide was added. Ethyl acetate was added and the solution was washed with water (3×50 mL). The organic layer was dried over magnesium sulfate, filtered, and the solvent removed in vacuo. Excess aniline was removed under vacuum at 90° C. overnight to give a crude product containing amine hardener [Structure (XII)].

The following analytical data was obtained for the resultant product:

IR (ATR): 3100-3500 (br, NH$_2$ amine stretch), 2800-3000 (br, C—H cyclic alkane stretch), 2600-1400 cm$^{-1}$ (aromatic skeletal vibrations).

HRMS (CI, ethyl acetate solution of the product): Mass calcd for C$_{32}$H$_{37}$N$_4$ [M+H]: 477.30. Found [M+H]:477.30. An additional peak was found at, 291.1845 consistent with isomers of Structure (III), mass calculated: 291.19. m/s ESI: Additional peaks were found including 581.3610, 777.4809, 871.5406. Potential structures of oligomeric condensation products consistent with these molecular weights are protonated Structures (IV)-(VII) and isomers of Structures (IV)-(VII).

Structure (III)

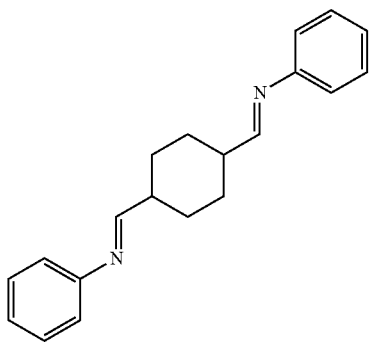

Structure (IV)
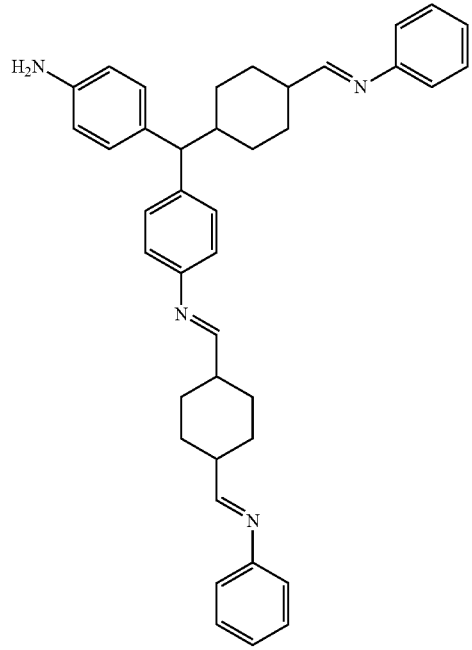
Chemical Formula: C₄₀H₄₄N₄
Exact Mass: 580.36
Structure (V)
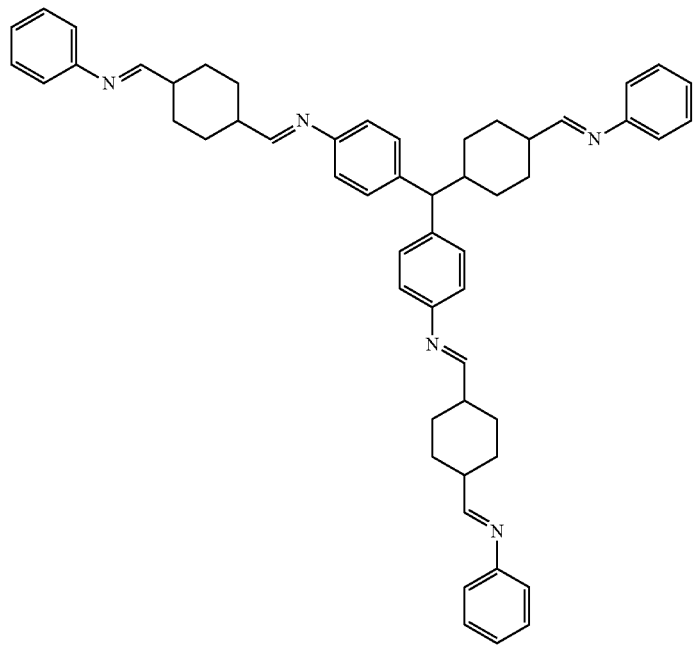
Chemical Formula: C₅₄H₅₉N₅
Exact Mass: 777.48

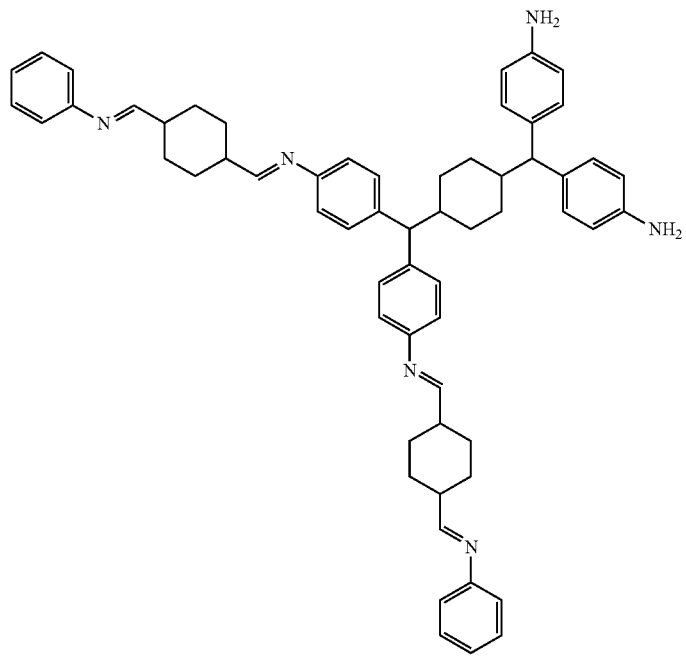

Chemical Formula: $C_{60}H_{66}N_6$
Exact Mass: 870.53

Structure (VI)

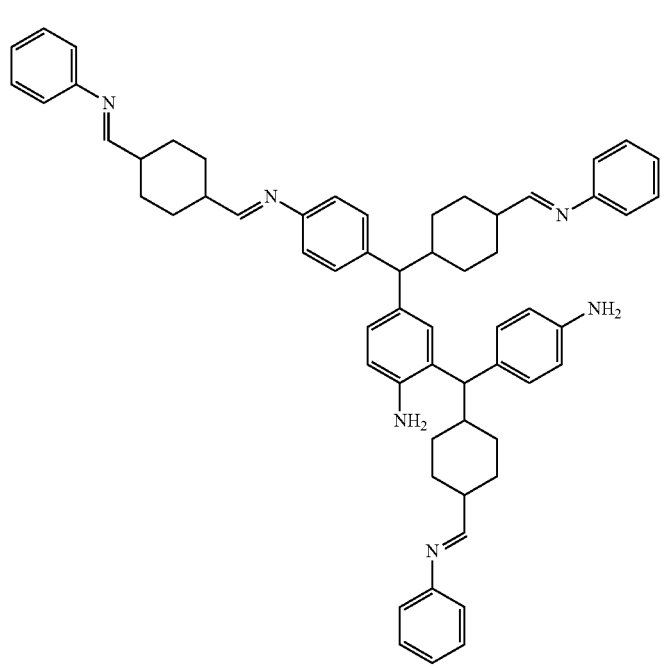

Chemical Formula: $C_{60}H_{66}N_6$
Exact Mass: 870.53

Structure (VII)

Example 2

The synthesis of an amine hardener composition was carried out, similar to

Example 1, as follows: Cyclohexane dicarboxaldehyde (10.0 g, 71.3 mmol, 1 equiv) and aniline (27.3 g, 292.8 mmol, 4.1 equiv) were added to a 250 mL two-necked round bottom flask equipped with a condenser and thermocouple. The flask was placed under nitrogen and 1.0 mL of concentrated hydrochloric acid was added. After refluxing at 110° C. for 5 hours, the reaction was allowed to cool to 50° C. and 1.5 mL of 50 wt % aqueous sodium hydroxide was added. Ethyl acetate was added and the solution was washed with water (3×30 mL). The organic layer was dried over magnesium sulfate, filtered, and the solvent removed in vacuo. Ethanol was added to the oil and stirred to precipitate the product as a light orange solid. The solid was collected via vacuum filtration and dried under vacuum at 70° C. to give a purified version of the product synthesized in Example 1.

Example 3

The synthesis of an amine hardener composition of the present invention was carried out as follows: DCPD dialdehyde (5.5 g, 28.6 mmol, 1 equiv) and aniline (12.0 g, 128.6 mmol, 4.5 equiv) were added to a 250 mL two-necked round bottom flask equipped with a condenser and thermocouple. The flask was placed under nitrogen and 0.5 mL of concentrated hydrochloric acid was added. After refluxing at 110° C. for 5 hours, the reaction was allowed to cool to 50° C. and 5 mL of 50 wt % aqueous sodium hydroxide was added. Ethyl acetate was added and the solution was washed with water (1×30 mL). The organic layer did not fully separate, but was dried over magnesium sulfate, filtered, and the solvent removed in vacuo. Excess aniline was removed by placing the solid under vacuum at 50° C. for 2 days to yield a glassy yellow solid. The lower molecular weight oligomers may also be removed by precipitating the product into hexanes prior to extraction.

The following analytical data was obtained for the resultant product in Example 3:

IR (neat): 3427 (br), 2943, 2869, 1619, 1562, 1511, 1413, 1273 cm$^{-1}$.

HRMS (ESI): Mass calculated for [M+H]: 529.33. Found [M+H]: 529.3341. Additional peaks were found including those consistent with isomers of the protonated Structures (VIII)-(X): 343.2185, 778.4875, 1027.6376.

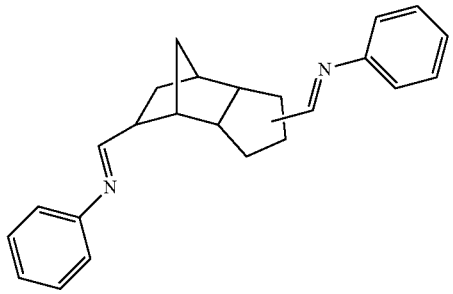

Structure (VIII)

Chemical Formula: $C_{24}H_{26}N_2$
Exact Mass: 342.21

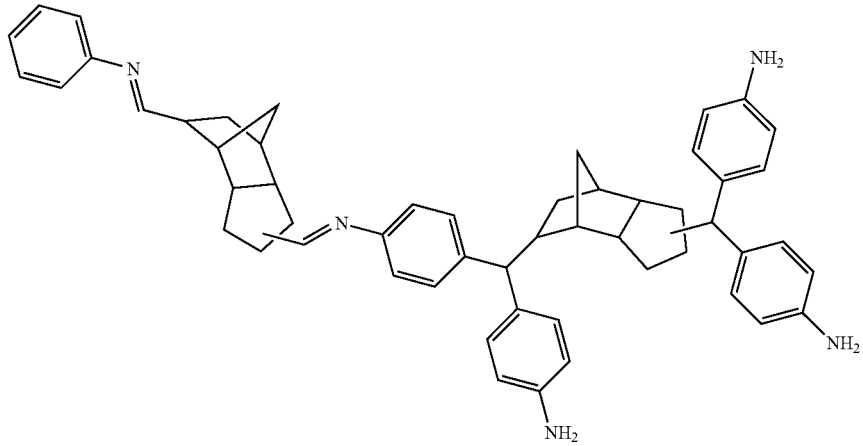

Structure (IX)

Chemical Formula: $C_{54}H_{59}N_5$
Exact Mass: 777.48

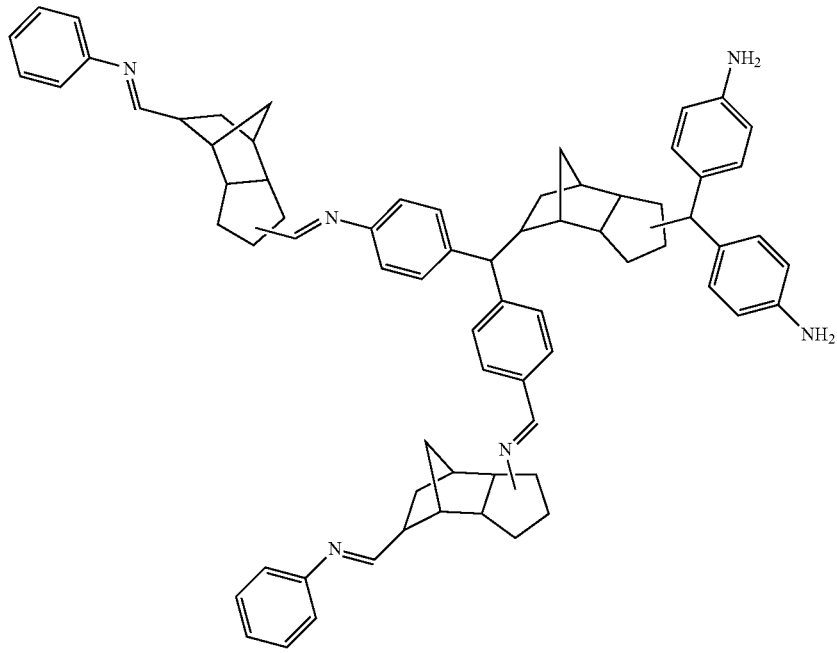

Structure (X)

Chemical Formula: $C_{72}H_{78}N_6$
Exact Mass: 1026.63

Example 4

The synthesis of a hardener composition of the present invention was carried out as shown in Equation (IX) as follows: The purified product from Example 1 (18.74 g, 39.3 mmol, 1 equiv) was dissolved in 25 mL $CH_2Cl_2$ in a round bottomed flask. Toluene (100 mL) was then added to the flask. Maleic anhydride (19.20 g, 195.8 mmol, 5 equiv) dissolved in 200 mL toluene was then added to the reaction solution. An orange solid precipitated and the reaction was stirred under nitrogen at room temperature for 2 hours. $ZnCl_2$ (26.2 g, 192.2 mmol, 5 equiv) was added to the reaction. Hexamethyldisilazane (61.5 mL, 294.9 mmol, 7.5 equiv) was then added dropwise over 30 minutes. The temperature was increased to 80° C. and the reaction was stirred for 1 hour under nitrogen. After cooling, the brown solid was collected via filtration, washed with hexanes, and dried in vacuo to give the product containing the maleimide.

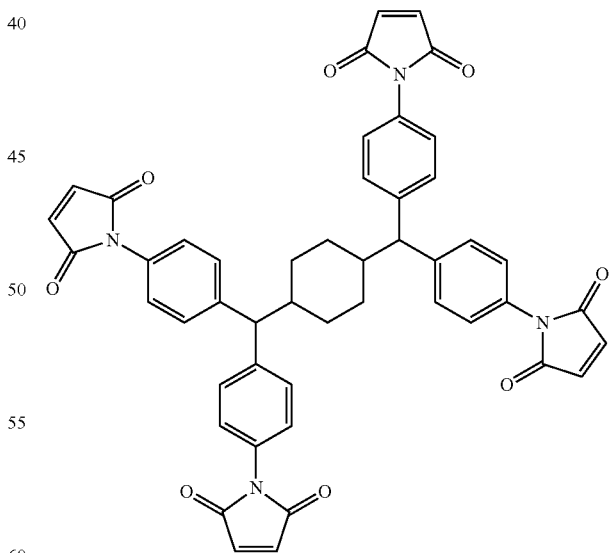

40

HRMS (CI): Mass calculated for [M+H]: 797.26. Found [M+H]: 797.26.

Example 5

The synthesis of a hardener was carried out as follows: maleic anhydride (1.25 g, 12.8 mmol, 2.5 equiv) was dissolved in 2 mL toluene in a round bottomed flask. 4,4'-(cyclohexylmethylene)dianiline (1.43 g, 5.1 mmol, 1 equiv) was dissolved in 3 mL toluene and added to the reaction, causing the intermediate amic acid to form as a yellow precipitate. ZnCl$_2$ (1.74 g, 12.8 mmol, 2.5 equiv) was added to the reaction. Hexamethyldisilazane (4.0 mL, 19.2 mmol, 3.75 equiv) was then added to the reaction over 30 minutes, after which the reaction was stirred under nitrogen at 80° C. for 1 hour. The solution was then poured into 100 mL of 0.5 M HCl, which formed a yellow precipitate. The aqueous solution was extracted with ethyl acetate (4×60 mL). The organic layer was washed with saturated NaHCO$_3$ (aq) (1×50 mL) and saturated NaCl (aq) (1×50 mL). The organic layer was dried over MgSO$_4$, and the solvent removed in vacuo to yield a bright yellow solid.

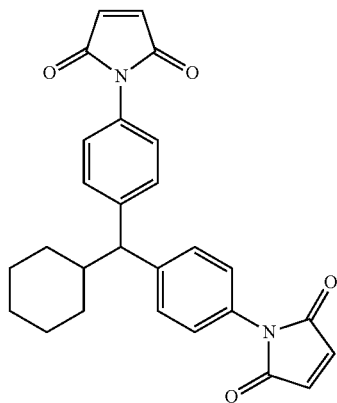 [SMILES: O=C1C=CC(=O)N1c1ccc(C(c2ccc(N3C(=O)C=CC3=O)cc2)C2CCCCC2)cc1]

The following analytical data was obtained for the resultant product synthesized in Example 5:
$^1$H NMR (300 MHz, CDCl$_3$) δ 7.33 (dd, 8H,) 6.85 (s, 4H), 3.59 (d, 1H), 2.11 (m, 1H), 1.80-0.77 (m, 10 H).

Preparation of Masterblends of Amine Hardener Compositions

Masterblend 1

An amount of 7 grams (g) of the product from Example 2 was dissolved in 7 g of 2-butanone to produce a 50% solids solution.

Masterblend 2

An amount of 10 g of 2-ethyl 4-methylimidazole was dissolved in 90 g of 2-butanone.

Masterblend 3

An amount of 7 g of 4,4'methanediyldianiline (MDA) and 7 g of 2-butanone were added to a 20 mL scintillation vial, placed on a shaker, and shaken on low speed for 60 minutes.

Masterblend 4

An amount of 8.5 g of D.E.R.* 332 and 1.5 g of 2-butanone were added to a 20 mL scintillation vial, placed on a shaker, and shaken on low speed for 60 minutes.

Masterblend 5

An amount of 7 g of the product from Example 1 was dissolved in 7 g of 2-butanone to produce a 50% solids solution.

Masterblend 6

An amount of 7 g of the product from Example 3 was dissolved in 7 g of 2-butanone to produce a 50% solids solution.

Masterblend 7

An amount of 7 g of 4,4'-(cyclohexylmethylene)dianiline was dissolved in 7 g of 2-butanone to produce a 50% solids solution.

Preparation of Thermoset Formulations

Comparative Example B

An amount of 3.93 g (0.0197 moles of epoxy) of D.E.N. 438EK85, 1.86 g (0.0187 moles amine hydrogen) of Masterblend 3, and 0.10 g of Masterblend 2 were added to a 20 mL scintillation vial and placed on a shaker on low speed for 30 minutes.

Comparative Example C

An amount of 3.93 g (0.019652 moles of epoxy) of Masterblend 4, 1.86 g (0.018716 moles amine hydrogen) of Masterblend 3, and 0.10 g of Masterblend 2 were added to a 20 mL scintillation vial and placed on a shaker on low speed for 30 minutes.

Comparative Example D

An amount of 3.02 g of D.E.N. 438EK85, 2.88 g of Masterblend 7, and 0.10 g of Masterblend 2 were added to a 20 mL scintillation vial and placed on a shaker on low speed for 30 minutes.

Example 6

An amount of 3.75 g of D.E.N. 438EK85, 2.14 g of Masterblend 1, and 0.10 g of Masterblend 2 were added to a 20 mL scintillation vial and placed on a shaker on low speed for 30 minutes.

Example 7

An amount of 3.18 g of D.E.N. 438EK85, 2.72 g of Masterblend 1, and 0.10 g of Masterblend 2 were added to a 20 mL scintillation vial and placed on a shaker on low speed for 30 minutes.

Example 8

An amount of 2.75 g of D.E.N. 438EK85, 3.15 g of Masterblend 1, and 0.10 g of Masterblend 2 were added to a 20 mL scintillation vial and placed on a shaker on low speed for 30 minutes.

Example 9

An amount of 2.43 g of D.E.N. 438EK85, 3.47 g of Masterblend 1, and 0.10 g of Masterblend 2 were added to a 20 mL scintillation vial and placed on a shaker on low speed for 30 minutes.

Example 10

An amount of 2.18 g of D.E.N. 438EK85, 3.73 grams of Masterblend 1, and 0.10 g of Masterblend 2 were added to a 20 mL scintillation vial and placed on a shaker on low speed for 30 minutes.

Example 11

An amount of 2.43 g of Masterblend 4, 3.47 g of Masterblend 1, and 0.10 g of Masterblend 2 were added to a 20 mL scintillation vial and placed on a shaker on low speed for 30 minutes.

Example 12

An amount of 2.18 g of Masterblend 4, 3.73 g of Masterblend 1, and 0.10 g of Masterblend 2 were added to a 20 mL scintillation vial and placed on a shaker on low speed for 30 minutes.

Example 13

An amount of 3.13 g of D.E.N. 438EK85, 1.79 g of Masterblend 5, and 0.10 g of Masterblend 2 were added to a 20 mL scintillation vial and placed on a shaker on low speed for 30 minutes.

Example 14

An amount of 2.65 g of D.E.N. 438EK85, 2.27 g of Masterblend 5, and 0.10 g of Masterblend 2 were added to a 20 mL scintillation vial and placed on a shaker on low speed for 30 minutes.

Example 15

An amount of 2.30 g of D.E.N. 438EK85, 2.62 g of Masterblend 5, and 0.10 g of Masterblend 2 were added to a 20 mL scintillation vial and placed on a shaker on low speed for 30 minutes.

Example 16

An amount of 2.03 g of D.E.N. 438EK85, 2.89 g of Masterblend 5, and 0.10 g of Masterblend 2 were added to a 20 mL scintillation vial and placed on a shaker on low speed for 30 minutes.

Example 17

An amount of 1.81 g of D.E.N. 438EK85, 3.11 g of Masterblend 5, and 0.10 g of Masterblend 2 were added to a 20 mL scintillation vial and placed on a shaker on low speed for 30 minutes.

Example 18

3.02 g of D.E.N. 438EK85, 1.90 g of Masterblend 6, and 0.10 g of Masterblend 2 were added to a 20 mL scintillation vial and placed on a shaker on low speed for 30 minutes.

Example 19

An amount of 2.52 g of D.E.N. 438EK85, 2.40 g of Masterblend 6, and 0.10 g of Masterblend 2 were added to a 20 mL scintillation vial and placed on a shaker on low speed for 30 minutes.

Example 20

An amount of 2.20 g of D.E.N. 438EK85, 2.72 g of Masterblend 6, and 0.10 g of Masterblend 2 were added to a 20 mL scintillation vial and placed on a shaker on low speed for 30 minutes.

Example 21

An amount of 1.95 g of D.E.N. 438EK85, 2.97 g of Masterblend 6, and 0.10 g of Masterblend 2 were added to a 20 mL scintillation vial and placed on a shaker on low speed for 30 minutes.

Example 22

An amount of 1.75 g of D.E.N. 438EK85, 3.17 g of Masterblend 6, and 0.10 g of Masterblend 2 were added to a 20 mL scintillation vial and placed on a shaker on low speed for 30 minutes.

Example 23

An amount of 1.6241 g of D.E.N. 438EK85, 1.2016 g of Primaset BA230s, 0.5983 g of the product of Example 5, 0.0254 g of zinc hexanoate, and 0.5760 g of 2-butanone were added to a 20 mL scintillation vial and placed on a shaker on low speed overnight. Gel time was 292 s, and Tg of the resulting material was 237° C.

Example 24

An amount of 4.13 g of D.E.N. 438EK85, 3.06 g of Primaset BA230s, 1.38 g of the product of Example 4, and 1.44 g of 2-butanone were added to a 20 mL scintillation vial and placed on a shaker on low speed overnight.

Analytical Data for Formulations of Examples 6-17

A 2 mL aliquot of each sample was placed on a 171° C. hotplate and agitated with a wooden applicator until gellation occurred according to IPC-TM-650 Number 2.3.18. The time to gellation was recorded for each sample. The gelled samples (scrapings) were removed from the hot plate and placed in a 190° C. oven for 90 minutes. A sample of the cured scraping was analyzed via differential scanning calorimetry (DSC) using a TA Instruments 2920 DSC with a nitrogen purge of 50 cubic centimeters per minute (cc/min). The profile consisted of a 20° C./minute ramp from room temperature to 300° C. The unused portions of the scrapings were then post cured for an additional 90 minutes at 220° C. and re-analyzed. The half extrapolated tangents analysis method was utilized to calculate the Tg.

TABLE I

Gel Time and DSC Tg Data for D.E.N. 438 Blends

| Property | Comparative Example B | 6 | 7 | 8 | 9 | 10 | 13 | 14 | 15 | 16 | 17 |
|---|---|---|---|---|---|---|---|---|---|---|---|
| Gel Time (sec) | 107 | 248 | 187 | 160 | 153 | 137 | 179 | 137 | 128 | 112 | 116 |
| Tg (deg C.), 190° C. Cure | 204 | 124 | 173 | 215 | 228 | 233 | 148 | 189 | 219 | 216 | 208 |
| Tg (deg C.), 220° C. Cure | 207 | 149 | 181 | 251 | 256 | 253 | 178 | 222 | 247 | 212 | 178 |

The data above from the blends with the precipitated product (Example 2) indicate a clear decreasing trend in gel time as the amine hydrogen molar content is increased in the formulation. In addition the DSC Tg data indicate significantly higher Tg valued for several of the blends containing the present invention hardener compared with the control which utilizes 4,4'methanediyldianiline at a 1.05 stoichiometric ratio with D.E.N. 438. The apparent amine hydrogen equivalent weight of the present invention hardener is calculated to be ~150 g/mol assuming the maximum Tg occurs at balanced stoichiometry likely a result of the imine concentration in the cured polymer.

The data from the blends with the crude product (Example 1) indicate a clear decreasing trend in gel time as the amine hydrogen molar content is increased in the formulation. In addition the DSC Tg data indicate significantly higher Tg values for several of the blends containing the present invention hardener compared with the control which utilizes 4,4'methanediyldianiline at a 1.05 stoichiometric ratio with D.E.N. 438. The data from the blends also indicate a maximum Tg at an apparent amine hydrogen equivalent weight of ~120 g/mol.

TABLE II

Gel Time and DSC Tg Data for D.E.R. 332 Blends

| Property | Comparative Example C | Example 11 | Example 12 |
|---|---|---|---|
| Gel Time (sec) | 260 | 293 | 256 |
| Tg (deg C.), 190° C. Cure | 186 | 207 | 220 |
| Tg (deg C.), 220° C. Cure | 187 | 235 | 229 |

The DSC Tg data indicate significantly higher Tg values for the blends containing the present invention hardener compared with the control which utilizes 4,4'methanediyldianiline at a 1.05 stoichiometric ratio with D.E.R. 332.

Analytical Data for Formulations of Examples 18-22

Several 10 cm by 15 cm pieces of 7628 glass (JPS Glass Fabrics) cloth with CS-718 sizing were cut and placed on a release sheet. Approximately 5 mL of the formulations were poured onto the glass, then spread using a wooden tongue depressor to wet the glass. The samples were placed into a 170° C. oven for 180 seconds and then placed into a 190° C. oven for 90 minutes. A sample was cut from the sheet for analysis and the remainder was placed into a 220° C. oven for an additional 90 minutes. The samples were cut into 1.27 cm wide by 2.0 cm long strips and analyzed via 3-point bend (10 mm span) utilizing a Rheometric Scientific RSA III. The procedure included a dynamic temperature ramp from 30° C. to 385° C. at 5° C./min at a frequency of 1 Hz and a strain of 0.1%. The Tg was assigned as the maximum in the tan δ data (max tan δ).

TABLE III

RSA Tg Data for D.E.N. 438 and DCPD-TA Blends

| max tanδ | Comparative Example A | Example 18 | Example 19 | Example 20 | Example 21 | Example 22 |
|---|---|---|---|---|---|---|
| Tg (deg C.), 190° C. Cure | 193 | 157 | 209 | 227 | 246 | 255 |
| Tg (deg C.), 220° C. Cure | 193 | 206 | 239 | 259 | 262 | 266 |

The max tan δ data for the DCPD-tetra amine (TA) blends (Examples 18-22) indicate significantly higher Tg values for the cured blends with the present invention hardener compared with the control which utilizes 4,4'methanediyldianiline at a 1.05 stoichiometric ratio with D.E.N. 438. The data indicate a maximum Tg at an apparent amine hydrogen equivalent weight of ~190 g/mol for the present invention hardener.

Advantages of Amine Hardeners Derived from Dialdehydes vs Monoaldehydes

The glass transition temperature of a cured thermoset from a dianiline compound derived from the monoaldehyde cyclohexane carboxaldehyde [Comparative Example A, Structure (XI)] is compared to cured thermosets from two polyaniline compounds derived from dialdehydes [Example 1, Structure (XII); and Example 3, Structure (XIII)]. When Comparative Example A, Example 1 and Example 3, are independently cured with an epoxy novolac as described in Comparative Example D, Example 14, and Example 21, the resultant Tgs are 216° C., 247° C. and 266° C., respectively. It is apparent that much higher Tgs can be obtained with the two polyanilines of Structures (XII) and (XIII).

Structure (XI)

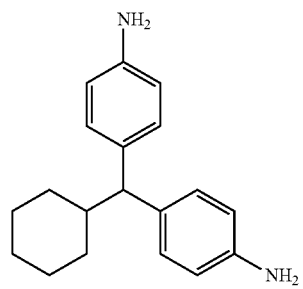

Structure (XII)

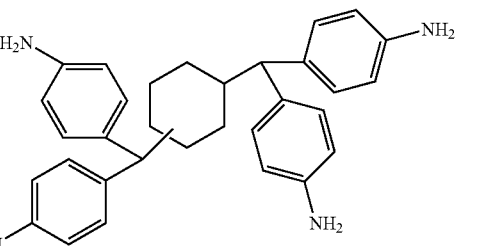

Structure (XIII)

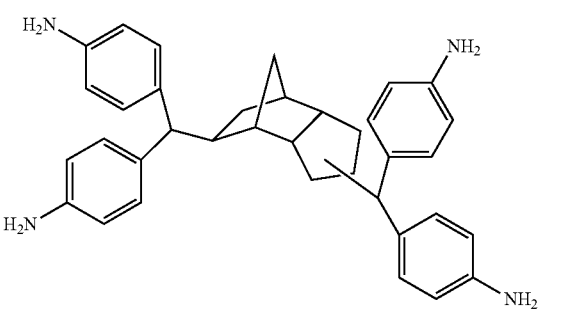

What is claimed is:

1. A multifunctional aromatic amine hardener composition of Structure (I) comprising the reaction product of (a) at least one aniline; and (b) at least one non-aromatic cyclic or polycyclic dicarboxaldehyde:

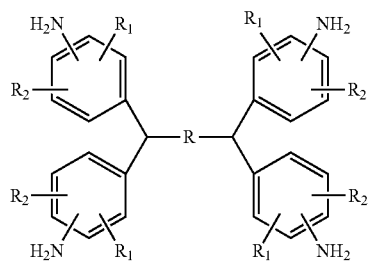
(Structure I)

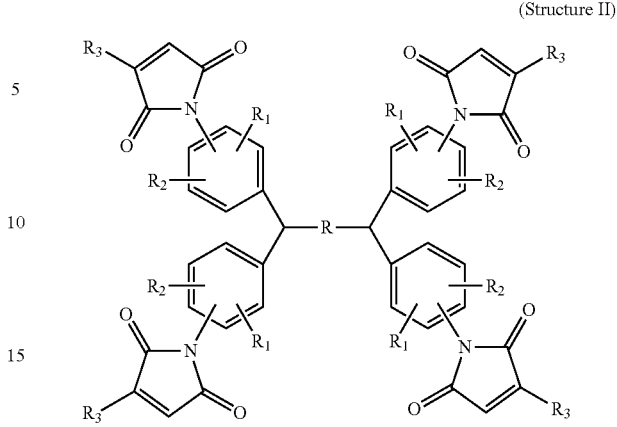
(Structure II)

wherein R in Structure (I) is a cycloaliphatic diradical and $R_1$ and $R_2$ are independently hydrogen, methyl, ethyl, i-propyl, n-propyl, n-butyl, i-butyl, t-butyl, methoxy, bromine, chlorine, fluorine, trifluoromethyl, methoxy, or ethoxy.

2. The composition of claim 1, wherein the non-aromatic cyclic dicarboxaldehyde comprises cyclohexane dicarboxaldehyde.

3. The composition of claim 1, wherein the non-aromatic polycyclic dicarboxaldehyde comprises dicyclopentadienedicarboxaldehyde.

4. A multifunctional maleimide composition of Structure (II) derived from the composition of claim 1:

wherein R in Structure (II) is a cycloaliphatic diradical, $R_1$ and R2 are independently hydrogen, methyl, ethyl, i-propyl, n-propyl, n-butyl, i-butyl, t-butyl, methoxy, bromine, chlorine, fluorine, trifluoromethyl, methoxy, or ethoxy, and $R_3$ is hydrogen or a hydrocarbon radical containing from 1 to 6 carbons.

5. A reactive thermosettable resin composition comprising (i) at least one hardener composition of claim 1, (ii) at least one thermoset resin, and optionally (iii) at least one catalyst.

6. The composition of claim 5, wherein the thermoset resin comprises an epoxy resin.

* * * * *